US006079252A

United States Patent [19]
Tabler et al.

[11] Patent Number: 6,079,252
[45] Date of Patent: Jun. 27, 2000

[54] LEAK DETECTION DEVICE, AND FLUID VESSEL ASSEMBLY COMPRISING SAME

[75] Inventors: Terry A. Tabler, Sandy Hook; Steven M. Lurcott, Sherman, both of Conn.

[73] Assignee: Advanced Technology Materials, Inc., Danbury, Conn.

[21] Appl. No.: 09/082,269

[22] Filed: May 20, 1998

[51] Int. Cl.[7] .............................. G01M 3/00; G01K 7/00; G01N 27/00; G01N 3/10
[52] U.S. Cl. ................................ 73/40; 73/24.1; 73/49.3; 73/592; 340/605
[58] Field of Search ........................ 73/40, 24.01, 40.5 R, 73/49.2, 49.3, 52, 40.5 A, 24.04, 592, 31.05, 31.06; 340/605

[56] References Cited

U.S. PATENT DOCUMENTS

| | | | |
|---|---|---|---|
| Re. 35,544 | 7/1997 | Snow | 73/24.01 |
| 3,534,587 | 10/1970 | Grenci et al. | 73/49.8 |
| 3,744,296 | 7/1973 | Beltzer | 436/142 |
| 4,020,784 | 5/1977 | Green et al. | 116/114 PV |
| 4,056,803 | 11/1977 | White et al. | 340/15 |
| 4,163,384 | 8/1979 | Blakemore | 73/29 |
| 4,349,282 | 9/1982 | Norfolk | 374/183 |
| 4,399,686 | 8/1983 | Kindlund et al. | 73/23 |
| 4,419,884 | 12/1983 | Grenci et al. | 73/49.8 |
| 4,446,720 | 5/1984 | Sinclair | 73/24.06 |
| 4,637,987 | 1/1987 | Minten et al. | 436/151 |
| 4,730,478 | 3/1988 | Gedeon | 73/23.21 |
| 4,735,081 | 4/1988 | Luoma et al. | 73/23 |
| 5,018,380 | 5/1991 | Zupanic et al. | 73/23.2 |
| 5,037,624 | 8/1991 | Tom et al. | 423/210 |
| 5,042,288 | 8/1991 | Vig | 73/24.01 |
| 5,056,355 | 10/1991 | Hepher | 73/24.03 |
| 5,065,140 | 11/1991 | Neuburger | 340/634 |
| 5,095,736 | 3/1992 | Fesler et al. | 73/23.2 |
| 5,101,657 | 4/1992 | Lahlouh et al. | 73/40.5 R |
| 5,138,869 | 8/1992 | Tom | 73/31.03 |
| 5,140,847 | 8/1992 | Tausch et al. | 73/40 |
| 5,151,110 | 9/1992 | Bein et al. | 95/140 |
| 5,151,395 | 9/1992 | Tom | 502/67 |
| 5,173,684 | 12/1992 | Tjiri et al. | 340/605 |
| 5,208,162 | 5/1993 | Osborne et al. | 436/6 |
| 5,320,817 | 6/1994 | Hardwick et al. | 423/237 |
| 5,325,705 | 7/1994 | Tom | 73/31.03 |
| 5,339,675 | 8/1994 | DiLeo et al. | 73/24.04 |

(List continued on next page.)

FOREIGN PATENT DOCUMENTS

| | | | |
|---|---|---|---|
| 6-308008 | 11/1994 | Japan | 73/24.01 |

OTHER PUBLICATIONS

Neuburger, Glen G., "Detection of Ambient Hydrogen Chloride with a Zinc–Coated Piezoelectric Crystal Resonator Operating in a Frequency–Time Different Mode," Anal. Chem. 1989, 61, 1559–1563.

Levenson, Leonard L., "II. Chemisorption on Single Element Thin Films," in *Applications of Piezoelectric Quartz Crystal Microbalances*, C. Lu, editor, vol. 7, Elsevier, Amsterdam, 1994, pp. 198–203.

"The World's First 8–Bit RISC MCU in an 8–Pin Package," Microchip Technology, Inc., Jun. 29, 1997, 2 pgs.

"SA612A Double–balanced mixer and oscillator," Philips Semiconductors, Nov. 7, 1997, 12 pgs.

*Primary Examiner*—Hezron Williams
*Assistant Examiner*—J. David Wiggins
*Attorney, Agent, or Firm*—Steven J. Hultquist; William A. Barrett; Oliver A. M. Zitzmann

[57] ABSTRACT

A leak detection device securable in detection proximity to a fluid vessel. The leak detection device includes a sensor element and a monitoring assembly. The sensor element has a monitorable characteristic, and the monitorable characteristic changes upon contact, immerson or in exposure to the fluid contained in the vessel. The monotoring assembly is responsive to the monitorable characteristic and produces an changing electrical output in response to change in the monitorable characteristic. The vessel and leak detection device may form an assembly including a shroud or cover over the detection device and a leak-susceptible portion of the vessel, to provide a microenvironment in which the detection device is operated.

75 Claims, 4 Drawing Sheets

U.S. PATENT DOCUMENTS

| | | | |
|---|---|---|---|
| 5,341,128 | 8/1994 | Keyser et al. | 340/605 |
| 5,378,995 | 1/1995 | Kudo et al. | 324/693 |
| 5,385,689 | 1/1995 | Tom et al. | 252/194 |
| 5,411,709 | 5/1995 | Furuki et al. | 422/91 |
| 5,417,821 | 5/1995 | Pyke | 204/153 |
| 5,445,008 | 8/1995 | Watcher et al. | 73/24.06 |
| 5,476,002 | 12/1995 | Bowers et al. | 73/24.01 |
| 5,518,528 | 5/1996 | Tom et al. | 95/103 |
| 5,573,728 | 11/1996 | Loesch et al. | 442/90 |
| 5,659,296 | 8/1997 | Debe et al. | 340/632 |
| 5,661,226 | 8/1997 | Bowers et al. | 73/24.01 |
| 5,705,399 | 1/1998 | Larue | 436/501 |

LEAK DETECTION DEVICE, AND FLUID VESSEL ASSEMBLY COMPRISING SAME

BACKGROUND OF THE INVENTION

1. Field of the Invention

This invention generally relates to leak detection devices and, more particularly, to a device useful for detecting low/trace concentration fluid components leaking from a fluid storage vessel, and to a fluid storage vessel assembly comprising such leak detection device. The leak detection device of the invention has utility, inter alia, as an environmental monitor for detection of hazardous gases during transport, storage and use of fluid storage vessels containing such gases.

2. Description of the Related Art

In the field of environmental gas monitoring, various means have been employed and/or proposed for the detection of low or trace concentrations of impurities, e.g., hazardous gas species, in air or other ambient gases.

The systems currently commercially available, such as the so-called MDA monitors or Kitagawa tubes, have basic design and operational deficiencies that limit their use. They are either costly, require significant maintenance (involving replacement of consumable elements, e.g., the frequent change of color tapes in MDA monitors), require frequent recalibration, or in some instances do not to measure the impurity species properly or provide useful readouts. The MDA monitor is sensitive only down to concentration levels on the order of about 5 ppm, and readings below that level are inaccurate.

These conventional types of environmental monitoring systems are fundamentally inapplicable to fluid storage vessels.

Thousands of fluid storage vessels, such as conventional gas cylinders, are handled, transported, and used to dispense fluids daily. Many of such fluid storage vessels contain toxic chemicals that are injurious to health and/or the environment if inadvertently or accidentally leaked to the ambient surroundings. There is, however, no known leak detection device designed for use with such fluid storage vessels.

The high cost and significant maintenance of MDA monitors and Kitagawa tubes render them cost-prohibitive for use with conventional gas cylinders. MDA monitors and Kitagawa tubes are also not physically robust, and thus are susceptible to being readily damaged even if they were otherwise fundamentally modifiable for use with conventional fluid storage vessels. The high maintenance required of MDA monitors and Kitagawa tubes, furthermore, renders these monitoring systems inapplicable to the highly mobile infrastructure and orientation of the gas cylinder industry.

In current practice, gas sampling devices (termed "sniffers") are typically used to sample the air or ambient gas in a railroad car, transshipment container, truck bed container, gas cabinet or other enclosure in which the gas cylinder is transported or stored, before the cylinder is placed into use. The sampled gas then is subjected to gas analysis for determination of the potential presence of hazardous gas species. This is time-consuming, requires significant effort and resources, and is inefficient.

There is, accordingly, a significant need in the art for a leak detection device which is accurate and reliable, which is easily fabricated and operated, and which is cost-effective, for use with fluid storage vessels such as gas storage cylinders.

Relative to the aspect of the invention hereinafter described and claimed, wherein the leak detection device of the invention comprises a piezoelectric crystal detector, relevant art includes the following:

U.S. Reissue Patent 35,544 to J. T. Snow (piezoelectric material having moisture-reactive metal oxide coating for detection of moisture in gas stream);

U.S. Pat. No. 5,339,675 to Anthony J. DiLeo, et al. (piezoelectric material having a metal and/or metal hydride coating, for detection of oxygen and/or water in a gas stream);

U.S. Pat. No. 5,661,226 to W. D. Bowers, et al. (surface acoustic wave monitor for detecting non-volatile residue contamination of an environment);

U.S. Pat. No. 5,411,709 to Makoto Furuki, et al. (fluorescent/phosphorescent gas-sensitive film on piezoelectric element, irradiated to generate light output indicative of gas concentration);

U.S. Pat. No. 5,061,140 to G. G. Neuburger (reactive gas detection system including array of quartz microbalance detectors coated with layer of zinc or zinc compound reactive with halogen gases);

U.S. Pat. No. 5,056,355 to M. J. Hepher (piezoelectric crystal sensor for monitoring dust or particulates in gas stream);

U.S. Pat. No. 4,730,478 to Andras Gedeon (gas component sensor including piezoelectric crystal with a surface layer of material for reversibly adsorbing the gas component);

U.S. Pat. No. 4,637,987 to Karl Minten, et al. (gas sensor including piezoelectric element coated with film of manganese tertiary phosphine polymer complex for absorbing gas);

U.S. Pat. No. 4,399,686 to A. R. Kindlund, et al. (piezoelectric crystal coated with silicone oil, preferably a silicone oil comprising a silicone glycol copolymer, for adsorption and sensing of halogenated hydrocarbons, e.g., anaesthetic gases such as halothane, enfluorane, metoxyfluorane and isofluorane); and U.S. Pat. No. 4,163,384 to C. B. Blakemore (moisture analyzer for measuring moisture in acid gas stream, including a piezoelectric crystal coated with polystyrene sulfonic acid or salt thereof, in which the coating has been stabilized by exposure to acid gas).

SUMMARY OF THE INVENTION

The aforementioned problems of the prior art are resolved by a leak detection device securable on or in proximity to a fluid vessel, preferably in leak detection proximity to a valve head or other dispensing portion of the vessel to constitute a fluid storage and dispensing assembly comprising the vessel and associated leak detection device.

In one aspect, the invention relates to a leak detection device, securable in detection proximity to a vessel, comprising:

a sensor element having a monitorable characteristic that changes in exposure to the content of the vessel; and a self-contained monitoring unit operatively coupled to the sensor element and arranged to respond to a change in the monitorable characteristic of the sensor element, by responsively producing an output indicative of the change in the monitorable characteristic.

In another aspect, the present invention relates to a fluid vessel assembly, comprising:

a fluid vessel; and a leak detection device secured in detection proximity to the vessel, said leak detection device comprising:

a sensor element having a monitorable characteristic that changes in exposure to the content of the vessel; and a self-contained monitoring unit operatively coupled to the sensor element and arranged to respond to a change in the monitorable characteristic of the sensor element, by responsively producing an output indicative of the change in the monitorable characteristic.

Other aspects and features of the present invention will be more fully apparent from the ensuing disclosure and appended claims.

DETAILED DESCRIPTION OF THE INVENTION, AND PREFERRED EMBODIMENTS THEREOF

Figure 1:
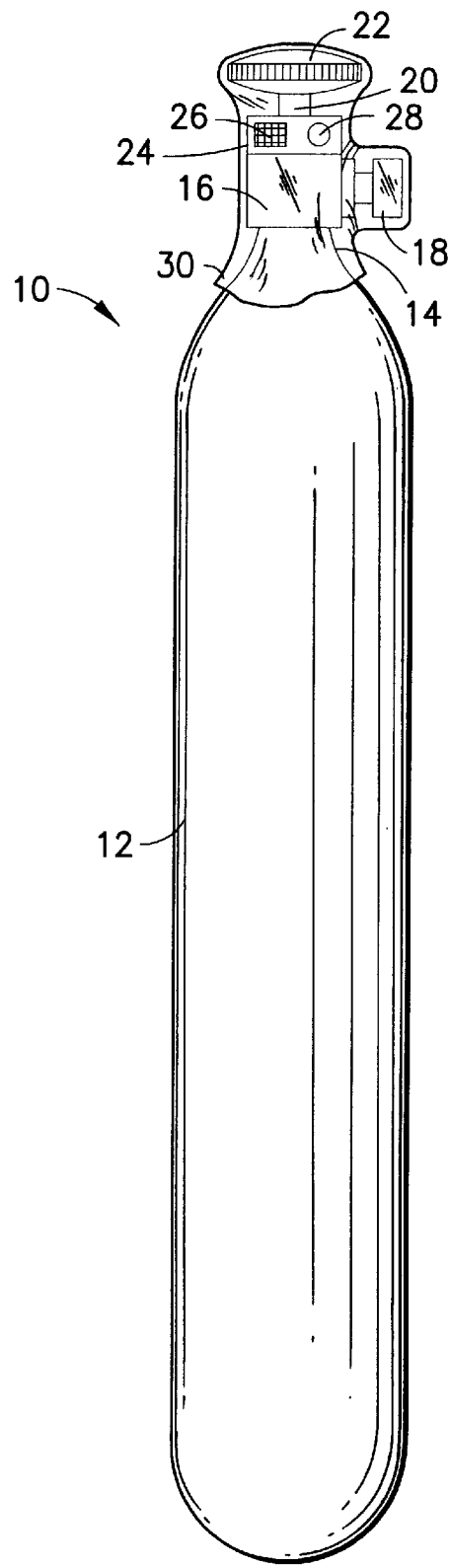
FIG. 1 is a front elevation view of a gas storage vessel and leak detector assembly according to one embodiment of the invention.

The disclosures of the following United States patents and patent applications are hereby incorporated herein by reference in their entirety: U.S. patent application No. 08/678,572 filed Jul. 12, 1996; U.S. patent application No. 08/679,258 filed Jul. 12, 1996; U.S. patent application No. 08/785,342 filed Jan. 17, 1997; U.S. Pat. No. 5,518,528 issued May 21, 1996 in the names of Glenn M. Tom and James V. McManus; and U.S. Pat. No. 5,704,965 issued Jan. 6, 1998 in the names of Glenn M. Tom, James V. McManus, and W. Karl Olander.

The present invention relates to a self-contained leak detection device that is securable in detection proximity to a vessel, i.e., on or near the vessel, to detect the presence of fluid incident to leakage from the vessel. As used herein, the term "self-contained" in reference to the leak detection device of the invention means that such leak detection device does not employ any external or remote power supply. The device therefore is unitary and self-sufficient in character. Preferably the leak detection device is mounted on the vessel. Such mounting may be effected by attachment means of any suitable type, e.g., mechanical fasteners such as bolt and nut assemblies, hang-type rings or loops by which the detector may be hung on the vessel, hook-and-loop fasteners that are securable about the circumference of the vessel, adhesive bonding securement, or other means which will not affect the integrity of said vessel, or the leak detection device may be configured so that the device overfits the neck or valve body of the vessel, so that the device fits under the manual handle (hand-wheel) or pneumatic valve operator of the valve on the vessel.

The vessel itself may be of any appropriate type, such as a high pressure gas cylinder for containing fluids such as hydride or acid gases for semiconductor manufacturing operations, e.g., arsine, phosphine, boron trifluoride, boron trichloride, silane, hydrogen fluoride, hydrogen selenide, diborane, or any other toxic, flammable or poisonous gas.

Alternatively, the vessel may be a container holding a liquid at superatmospheric pressure, or a container holding a solid having appreciable vapor pressure.

As a still further alternative, the vessel may contain a solid sorbent material on which a gas is sorptively retained, and from which the gas may be selectively desorbed for dispensing and use of the gas, as more fully described in U.S. Pat. No. 5,518,528 issued May 21, 1996 in the names of Glenn M. Tom and James V. McManus; and U.S. Pat. No. 5,704,965 issued Jan. 6, 1998 in the names of Glenn M. Tom, James V. McManus, and W. Karl Olander.

The leak detector of the invention includes a sensor element having a monitorable characteristic that changes in exposure to the content of the vessel. The content of the vessel may be susceptible to leaking from the vessel at its joints, seams, ports, inlets, outlets and mechanical interconnections. The leak detector therefore is correspondingly positioned to detect the presence of such fluid vessel content at such locations of possible egress from the vessel.

The leak detector also includes a self-powered monitoring unit operatively coupled to the sensor element and arranged to respond to a change in the monitorable characteristic of the sensor element, by responsively producing an output indicative of the change in the monitorable characteristic.

The monitorable characteristic of the sensor element includes at least one property such as resonant frequency, color, texture, chemical resistance, magnetic state, density, and/or chemical compositional state.

In a preferred aspect, the sensor element comprises a piezoelectric material. For example, the sensor element may comprise a quartz microbalance (QMB) or a surface acoustic wave (SAW) device, and the monitorable characteristic is the resonant frequency of the material.

The self-contained monitoring unit may include a power supply, such as an electrical power supply, e.g., a battery, photovoltaic cell, fuel cell, microgenerator, or the like. The power supply may include a DC power supply and/or an AC power supply. In a preferred aspect, the monitoring unit includes a battery power supply providing at least four months operating time in service, more preferably at least six months operating life, and most preferably has an operating life of at least one year.

The self-contained monitoring unit may be variously configured and constituted, depending on the specific vessel and fluid involved. For example, the monitoring unit may comprise a microprocessor embedded controller assembly, as well as any other microelectronics and circuitry elements, appropriate to the specific embodiment involved.

In a specific embodiment, the self-contained monitoring unit may include a power supply and electronic circuitry that are constructed and arranged to operate in an intermittently active mode, and in a power-down ("sleep") mode between successive active mode events.

The monitoring unit may include an alarm producing the output indicative of the change in the monitorable characteristic of the sensor element. Such alarm may include an audible alarm, a visual alarm, and/or a tactile alarm. The audible alarm may include a beeper, buzzer, siren, or any other sound source indicative of the alarm condition, viz., the presence of the fluid being monitored in the environment associated with the vessel. The visual alarm may include a flasher, light, strobe, electroluminescent element, phosphor, scintillation coating, or any other element(s) producing a visually discernible output indicative of the alarm condition. The tactile alarm may include a buzzer, oscillator, vibrator, or other touch- or kinesthetically-perceptible output indicative of the alarm condition.

In a specific embodiment, wherein the sensor element comprises a mass-sensitive piezoelectric device, the self-contained monitoring unit comprises an FM frequency oscillator/mixer coupled in frequency response-generating relationship to the piezoelectric device, so that the oscillator/mixer excites the piezoelectric device at an appropriate frequency and processes the resulting frequency response output.

The oscillator/mixer may for example be coupled to a low-pass filter to produce an output frequency response signal having a frequency below 100 kilohertz (kHz). A signal-processing microprocessor arranged in receiving relationship to the output frequency response signal, produces an output indicative of the change in the monitorable characteristic (the frequency response of the piezoelectric device).

The invention therefore contemplates a fluid vessel assembly including a vessel equipped with the leak detector device more fully hereinabove. The fluid vessel may contain a liquid, gas, and/or vapor at high pressure (e.g., superatmospheric pressure). The vapor may derive from a liquid or solid that is contained in the vessel and has an appreciable vapor pressure.

Where the fluid vessel includes a valve head structure, such as a valve head, connector for fluid dispensing lines, manual actuator (e.g., a hand wheel) or pneumatic valve operator, flow regulator, etc., the valve head structure may be provided with a shroud overlying the valve head structure. Such shroud protects the structure from dust, particulate contamination, moisture, and other components that may be deleterious in exposure to the valve head structure.

The shroud may be formed by a heat-shrinkable sleeve that is placed over the valve head structure and then heated, e.g., by a heat gun, to shrink the sleeve so that it generally conforms to the shape of the valve head structure. This is a widely practiced expedient for protecting the valve head structure of high pressure gas cylinders during transport and storage. The shroud defines an enclosed volume therewithin. The leak detection device of the invention may be disposed in such interior volume, so that any leakage from the valve head structure is contained by the interior volume within the shroud, and is quickly detected by the leak detection device.

In a preferred embodiment, the leak detection device is secured to the valve head and underlies the manual valve hand wheel or pneumatic valve operator. The leak detection device most preferably has a lateral extent that is generally not in excess of the lateral extent of the manual valve hand wheel or pneumatic valve operator, so that the valve head structure and the leak detection device together form a conjoint structure of a highly compact character. The leak detection device is suitably secured to the fluid vessel, as for example on the valve block.

The present invention in a preferred aspect utilizes piezoelectric crystals coated with electrode sensor materials such as thin metal film coatings of Cu, Zn, Ag, Al, Cr, etc., to provide highly sensitive detectors for gas species of interest, e.g., halide and hydride gases. When the gas contacts and reacts with the electrode sensor material under operating conditions, a change is produced (electrical resistivity, conductance, frequency response, etc.) which is processed by the monitoring unit to produce a correlative output indicative of the presence of the gas species of interest.

In the piezoelectric crystal sensor device of the invention, the piezoelectric crystal coated with the electrode sensor material is subjected to an input frequency, such as by means of an appropriately constructed and arranged oscillator circuit coupled in operative relationship to the piezoelectric crystal. The output frequency of the piezoelectric crystal coated with the electrode sensor material then is monitored and the change of the frequency in relation to the natural harmonic frequency of the coated crystal is determined, e.g., by a cascaded counter assembly.

By this arrangement, the contacting of halide gas with a suitable reactive metal coating material on the crystal will cause reaction to yield a metal-containing reaction product of different mass than the initial mass of the metal coating on the crystal. As a result of such mass change, the frequency response characteristics of the coated crystal will change, and this frequency change will reflect the presence of the specific component in the gas contacted with the coating film on the piezoelectric crystal. The frequency change can then be outputted to provide a suitable alarm (e.g., audible siren, visible light or strobe, infrared signal detector by a remote IR sensing unit, etc.) or other warning signal indicating the occurrence of fluid leakage from the vessel.

As mentioned, the leak detection device may for example include a housing or shroud by means of which a leak-susceptible portion of a vessel, or an assemblage of vessels manifolded or otherwise ganged together, may be placed in closed gas flow communication with the detection device.

By way of specific example, in the practice of the invention involving sensing of gaseous halide components, the frequency of an oscillator in a piezoelectric crystal circuit may be readily monitored to detect halogenation of the electrode, involving chemical reactions such as the following:

$$Zn+2HCl \rightarrow ZnCl_2+H_2$$

$$Zn+F_2 \rightarrow ZnF_2$$

It is readily feasible in the practice of the invention to tailor the reactivity of the coating material on the piezoelectric silica crystal, by choice of different materials, to obtain the appropriate desired sensitivity to different trace gases. For example, set out below are several illustrative thermodynamic equilibrium constants, for the reaction of HCl with different electrode (piezoelectric crystal coating) materials:

$$2HCl(g)+2Ag \rightarrow 2AgCl+H_2(g) \quad K_{eq}=10^6$$

$$2HCl(g)+2Cu \rightarrow CuCl+H_2(g) \quad K_{eq}=10^{17}$$

$$2HCl(g)+Zn \rightarrow ZnCl2+H_2(g) \quad K_{eq}=10^{35}$$

From the foregoing tabulation of reactions and equilibrium constants, one would predict that of these three piezoelectric crystal coating materials, Zn would be the most sensitive to HCl, and Ag would be the least. In like manner, a desired sensitivity coating material can readily be selected, for various other and specific gas components of interest, in a given sensing or monitoring application of the present invention.

In the preferred practice of the present invention, a piezoelectric crystal is used as a leak detection sensor element, and features a coating thereon of a material which is interactive with the gas species of interest, to yield an interaction product which alters the frequency response of the piezoelectric crystal, so that the presence of the gas species is readily detectable in the gas contacted with the coated crystal.

The coating material may suitably comprise a material which is irreversibly chemically reactive with the gas species of interest, to produce a reaction product which is of a different mass than the original coating material, being either greater or smaller in magnitude in relation to the virgin coating on the crystal. Alternatively, the coating on the piezoelectric device may be a material that is reversibly reactive or reversibly physically adsorptive of the gas species of interest, to yield the change in mass of the sensor element that is employed to generate the output indicative of the presence of the gas species in the environment being monitored by the detection device.

An important issue in the use and operation of the piezoelectric crystal detection sensor element is keeping particulates away from the sensor element. Maintaining the sensor element free of particulates avoids false alarms due to additional loading of the particulates on the crystal.

FIG. 1 is a front elevation view of a high pressure gas cylinder assembly 10 including a high pressure gas cylinder 12. The cylinder has a neck portion 14 on which is mounted a valve head including valve block 16 and gas dispensing line coupling 18.

Mounted on the spindle 20 of the valve head below hand wheel 22 is a leak detection device 24 according to the invention. The leak detection device 24 includes an audio alarm speaker 26 and a visual alarm light 28. As shown, the leak detection device 24 has a transverse or lateral extent (perpendicular to the longitudinal axis of the cylinder 12) that is somewhat smaller but still generally equivalent to the transverse extent of the hand wheel (as noted in this illustration) or pneumatic operator as per another embodiment, 22 of the valve head.

Overlying the valve head of the FIG. 1 cylinder is a shroud 30 of heat-shrinkable material such as a film of a polymeric, transparent, and heat-shrinkable material. The shroud thereby encloses a microenvironment in which the leak detection device 24 is disposed, so that any leakage from the neck portion of the cylinder, or mechanical connections within the valve head, will be very rapidly sensed by the detector to actuate the corresponding alarm.

Figure 2:
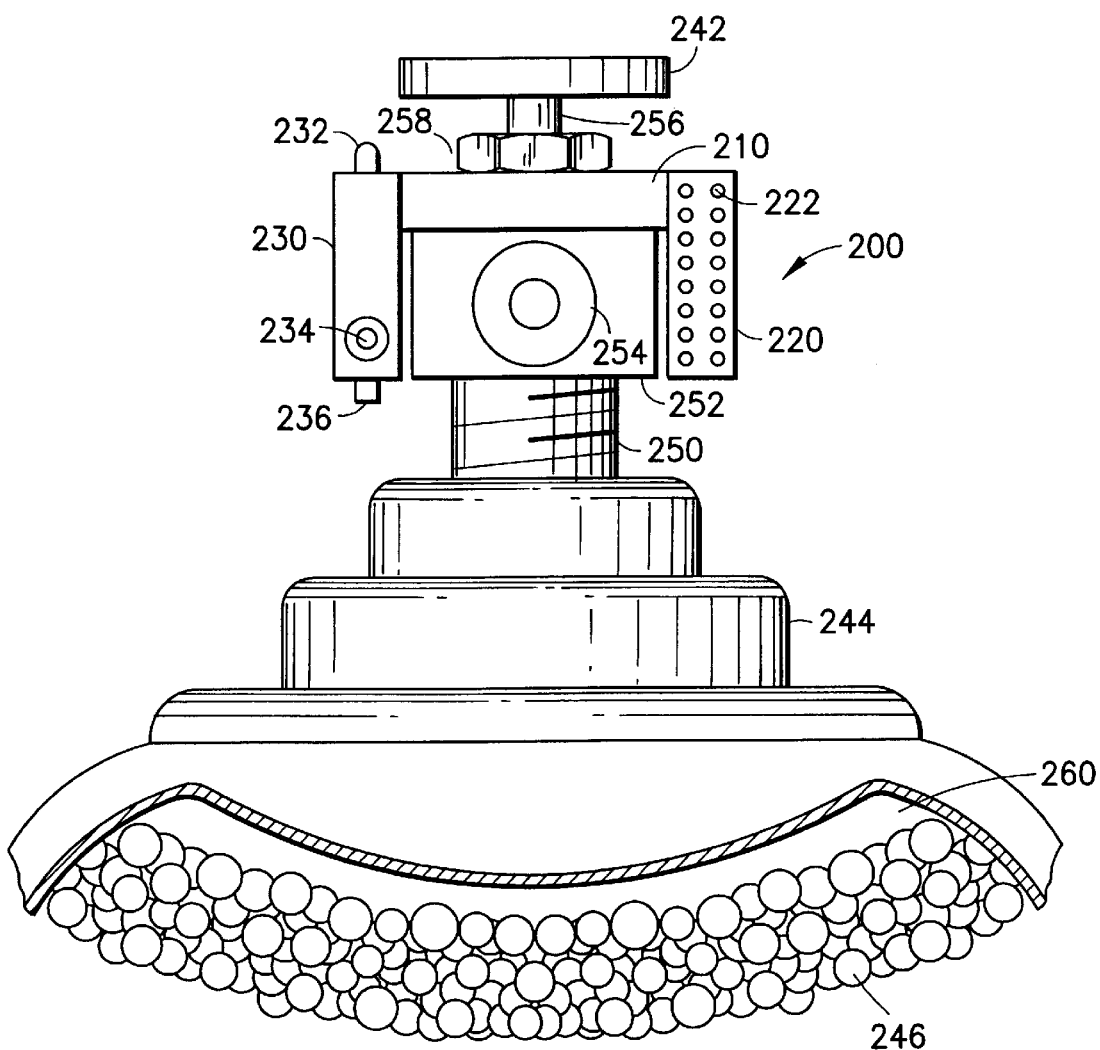
FIG. 2 is a front elevation view of a gas source vessel equipped with a leak detector according to another embodiment of the invention.

FIG. 2 shows a front elevation view of a gas storage and dispensing vessel 244 equipped with a leak detection device 200 according to a preferred embodiment of the invention. The vessel contains an interior volume 260 in which is provided a bed of a solid sorbent material 246. The solid sorbent material 246 has sorptive affinity for a gas which is to be stored in and selectively dispensed from the vessel, as more fully described in U.S. Pat. No. 5,518,528.

Above the neck 250 of the vessel 244 is a yoke or crossmember 210, overlying the valve block 252 containing valve discharge port 254. The yoke 210 of the detection device has a central opening therein (not shown) permitting the stem 256 of the valve associated with valve hand-wheel 242 to pass therethrough. The yoke 210 is secured in place beneath the hand wheel (as shown in the drawing) or pneumatic operator in an alternative embodiment, by a lock nut 258 engaging threads (not shown) on a lower threaded portion of the stem 256 for such purpose.

The sensor element housing 220 and the monitoring unit housing 230 are each mounted to the yoke as shown, to constitute therewith an inverted-U structure that compactly fits beneath the hand wheel 242 (as shown in the drawing) or pneumatic operator in an alternative embodiment. The sensor element housing 220 contains therein a piezoelectric crystal detector element (not shown) that is energized to generate a frequency response, and that is interactive with a gas species stored in vessel 244.

A chemisorbent or physical adsorbent coating is provided on the crystal. The coating materials that may be used for such purpose include the materials described in: U.S. patent application No. 08/678,572 filed Jul. 12, 1996; U.S. patent application No. 08/679,258 filed Jul. 12, 1996; and U.S. patent application No. 08/785,342 filed Jan. 17, 1997.

The coating on the crystal interacts with the gas species and alters the resonant frequency of the piezoelectric crystal, so that the presence of the gas species is readily detectable in the gas contacted with the coated crystal. Gas intake ports 222 may employed, through which the gas flows to the sensor element contained in the housing 220. Such gas intake ports or other flow limiting structures may be employed to force the flow to be purely or substantially diffusional in character and may be sized so that the ports act as a particle filter at the same time.

Monitoring unit housing 230 contains a monitoring assembly (not shown) and may optionally contain an alarm strobe 232, an audible alarm enunciator 234, and an alarm reset switch 236. The monitoring unit housing is electrically coupled with the sensor element housing by means of wiring therebetween that is passed through a via or passage (not shown) in crossmember 210.

The monitoring unit shown in FIG. 2 can be calibrated to output an alarm at a predetermined gas concentration. The alarm elements may have associated alarm limits, e.g., by programming of a microprocessor control in the monitoring unit, so that the alarms are actuated at or near the STEL (Short Term Exposure Limit) of the gas contained in the vessel, as defined by ACGIH/NIOSH standards. The monitoring unit may alternatively be calibrated to generate an output alarm at any suitable concentration determined by the user.

An alarm reset switch may be employed to deactivate the monitoring unit, and an optional discrete alarm contact port may be included for activating a remote alarm, such as for example by infrared signal generation to a remote output unit. Such remote output unit may for example be a remote computer unit receiving the infrared signal and generating a correlative alarm output. Alternatively, the remote output unit could be a beeper unit worn by an individual engaged in evaluating a multiplicity of such detector-equipped vessels to determine their amenability to safe handling for transport and use, and providing an audible output in response to the presence of any "leakers" in the fluid vessels being monitored.

Integral power source(s) (not shown) may be housed within the sensor element housing 220 and/or within the monitoring unit housing 230. The power sources usefully employed in the broad practice of the invention may include DC batteries, such as size AAA alkaline or lithium batteries. An AC adapter could be used for optional power supply to the leak detection device.

Battery life may be extended by the provision of appropriate control circuitry in the monitoring unit including a cycle timer or other control means that enable a "sleep mode" that only intermittently activates the device for fluid sensing duty. For example, the control circuitry may be arranged to actuate the leak detection device for active fluid sensing once every 5 or 10 minutes. An alarm may also be provided in the leak detection device to indicate low battery life.

The leak detection device 200 is desirably sized such that a standard gas cylinder valve cap fits over the device. Each of the sensor element housing 220 and the monitoring unit housing 230 may for example be about 2.5×2.5×0.5 inches in size.

The leak detection capabilities of the leak detection device 200 may be further enhanced by encapsulating the vessel valve head and associated leak detection device in shrink wrap, or a hood or shrouding structure (not shown for clarity in FIG. 2, but of the general type shown in FIG. 1). Such interior positioning of the leak detection device within a shroud provides a gas sensing microenvironment at the region of the valve head of the vessel where statistically the vast majority of leak events occur.

The leak detection device of the present invention may be usefully employed in various fluid storage vessel configurations. The leak detection device 200 can as described herein be affixed to the neck or valve head of a conventional gas cylinder. Likewise, the device could be affixed to a bulk storage tank, such as a ground or railroad tank car, or placed in leak sensing communication with multiple fluid storage vessels in a storage facility.

The leak detection device of the invention may as illustrated in FIG. 2 be employed with a sorbent-based gas storage and delivery system, including a gas storage and dispensing vessel containing a physical adsorbent material on which the gas to be dispensed is adsorbed. Gas storage and dispensing systems of such type are commercially available from ATMI, Incorporated of Danbury, Conn., under the trademark "SDS." The gas within the vessel in such sorbent-based systems may comprise any suitable gas species, including acetylene, germane, ammonia, phosphine, arsine, stibine, hydrogen sulfide, hydrogen selenide, hydrogen telluride, halide (chlorine, bromine, iodine, and fluorine) gases, etc.

The leak detection device of the present invention provides a simple and efficient means to provide unattended, safe and reliable monitoring of fluid storage vessels throughout the life cycle of the vessel. The manufacturer, transporter, reseller, end user and communities through which these vessels are transported and in which these vessels are used, may thereby minimize the danger and impact of a hazardous fluid release from the vessel, since the leak detection device may be set for very low threshold alarm conditions, so that the leaking fluid vessel is immediately isolatable for remedial action.

It will be appreciated that the sensor, housing, power source, and other componentry of the leak detection device of the present invention may assume a wide variety of conformations and arrangements, depending on the nature of the fluid vessel, and the desired operation of the leak detection device.

The device may for example include a compact housing containing the detection element and the monitoring components, that is directly affixable to a fluid storage vessel.

Alternatively, the device may include a housing containing the detection element and the monitoring components, that is mountable to a wall in near physical proximity to the fluid vessel being monitored.

The integral power source may include a DC power source, such as a dry or wet cell battery, for ease of use and portability. The power source may, alternatively, include an AC power source. The power source may also include an array of solar cells, to convert solar energy into electrical energy, for continuous monitoring of outdoor storage vessels.

Figure 3:
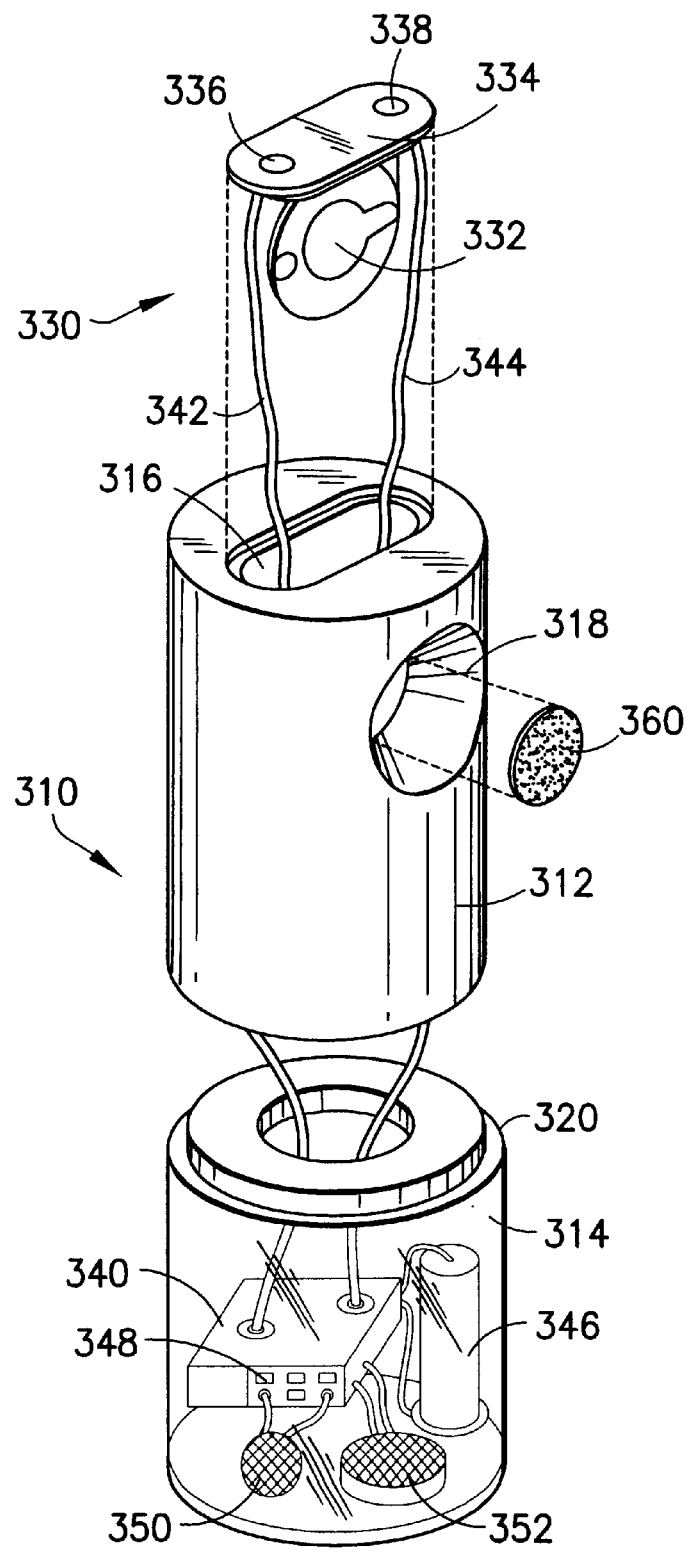
FIG. 3 is a schematic perspective view of a quartz microbalance leak detector according to still another embodiment of the invention.

FIG. 3 shows a perspective view of a leak detection device according to a specific embodiment of the invention. The device 300 includes housing 310 and sensor element 330. The housing 310 includes upper portion 312 and lower portion 314. The lower portion 314 removably engaged with the upper portion 312 at concentric shoulder 320.

The sensor element 330 comprises piezoelectric crystal 332 which is coated with a suitable material interacting with the fluid component of interest to yield an interaction product of differing mass characteristic than the original coating material. The coated crystal is mounted on the plug member 334. The respective leads of the piezoelectric crystal 332 protrude interiorly of the plug member when the plug member is engaged with the housing upper portion 312, with the coated crystal positioned in the cavity 316.

The housing upper portion 312 features a flow passage 318 by which a gas being monitored (e.g., a purge gas stream from a gas cabinet containing a fluid vessel holding a hazardous gas) can be flowed into the cavity 316 containing the sensor element 330. Although not shown in the perspective view of FIG. 3, the housing upper portion 312 has another passage opening therein, opposite opening 318 and in register with such opening, for discharge from the housing of the gas flowed past the coated piezoelectric crystal. Flow passage 318 may optionally include a flow limiting structure, such as frit 360, to keep particles in the gas stream being monitored from contacting the sensor element.

Leads 336 and 338 of the sensor element may be coupled in circuit relationship to suitable monitor assembly 340 in FIG. 3, by which the presence and concentration of the gas species of interest can be detected. The monitor assembly 340 is operatively coupled to the sensor element leads 336 and 338 by wires 342 and 344, respectively.

Monitor assembly 340 may be a microelectronics module and provides the functions of (i) sampling the output resonant frequency of the piezoelectric crystal while the oscillating electric field is applied thereto, (ii) determining any change in resonant frequency from the fundamental resonant frequency incident to the formation of an interaction product (when the gas species of interest interacts with the sensor element), and (iii) generating an output indicative of the presence of the gas species of interest in the fluid being monitored.

Housing upper portion 312 and lower portion 314, as shown in FIG. 3, may be constructed of plastic, such as rigid polyvinyl chloride or high density polyethylene, low density polyethylene, low density polypropylene, etc., or of a metal or composite material. The lower portion 314 is shown in FIG. 3 as having a housing formed of a transparent material of construction, to show the interior components of the lower portion.

The monitor assembly 340 is operatively coupled to the leads 336 and 338 of the sensor element 330. A power source 346, integral with the device, powers monitoring assembly 340. The resulting device 300 may be disposed in gas monitoring relationship to a fluid vessel to determine the presence of leak components of the fluid in the gas stream being monitored.

In the FIG. 3 device, alarm circuitry 348 (shown as a portion of monitoring assembly 340) is employed to activate a visual alarm 350, such as a light or strobe or display source, and the monitoring assembly 340 is additionally arranged to emit an audible alarm 352, in the event that a leak is determined to exist. The alarm circuitry could optionally be arranged to transmit an alarm signal to remote location(s) via a conventional signal cable or via wireless communications.

Figure 4:
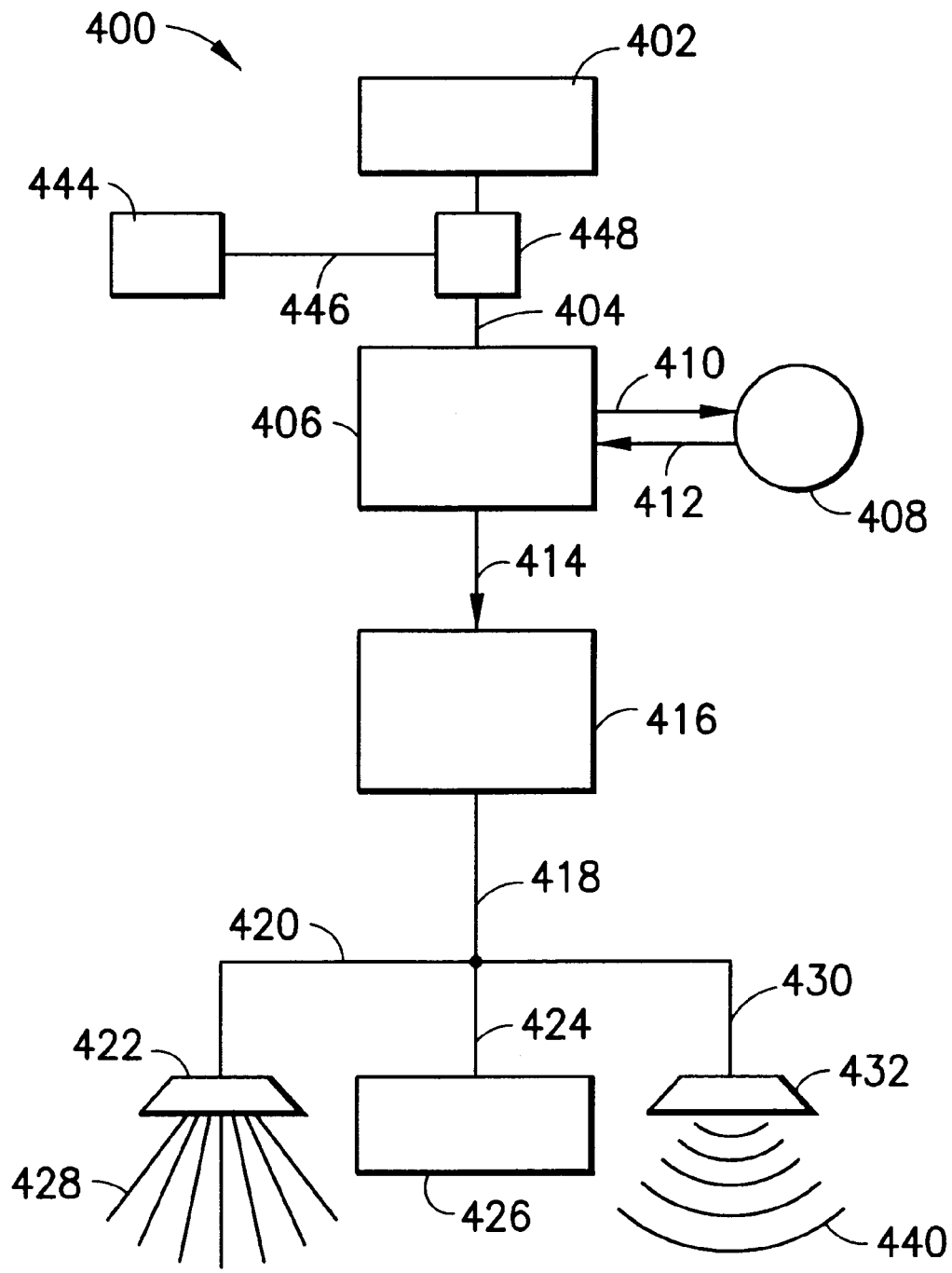
FIG. 4 is a schematic block diagram of a leak detector according to an illustrative embodiment of the present invention, including an oscillator/mixer and low pass filter.

FIG. 4 is a schematic representational block diagram of a leak detection device 400 according to an illustrative embodiment of the present invention, including an oscillator/mixer 406 and microprocessor/low pass filter unit 416, arranged as shown with respect to a piezoelectric crystal device 408.

The device includes a battery 402 interconnected by power supply wire 404 with the oscillator/mixer 406. A cycle time controller 444 is connected by signal transmission wire 446 to the switch 448, to effect intermittently actuated operation of the leak detection device, to conserve battery power and prolong the useful life of the detection device, e.g., for 6–12 months.

The oscillator/mixer 406 is joined to the piezoelectric crystal 408 to impart excitatory energy 410 to the crystal. As a result, the crystal produces an output 412 whose frequency response characteristics are used to generate an output signal 414 from the oscillator/mixer 406 to the microprocessor/low pass filter unit 416. The resulting filtered output 418 is passed, alteratively or concurrently, in output line 420 to visual alarm unit 422 to produce the visual output 428, in output line 430 to audio alarm unit 432 to produce the audible output 440, and/or in output line 424 to the central processing unit 426 for recordation or further processing of the output signal.

The oscillator/mixer in the above-described leak detection device may for example comprise an SA612A double-balanced mixer and oscillator unit commercially available from Philips Semiconductors (Sunnyvale, Calif.) operatively linked to an embedded microcontroller unit, e.g., a PIC 12C 8-pin microcontroller unit commercially available from Microchip Technology Inc. (Chandler, Ariz.). Other components are readily commercially available, and their use and deployment to provide a compact, robust leak detection device in accordance with the present invention may be readily effected within the skill of the art.

While the invention has been described herein with reference to specific aspects, features, and embodiments, it will be apparent that other variations, modifications, and embodiments are possible, and all such variations, modifications, and embodiments therefore are to be regarded as being within the spirit and scope of the invention.

What is claim is:

1. A leak monnotoring fluid storage and dispensing apparatus comprising:
   (a) a portable vessel having contents which comprise a hazardous gas; and
   (b) a leak detection device secured to the vessel and arranged to detect leakage of said hazardous gas therefrom, said leak detection device comprising:
       (i) a sensor element having a monitorable characteristic that changes upon exposure to the hazardous gas; and
       (ii) a self-contained monitoring unit operatively coupled to the sensor element and arranged to respond to a change in the monitorable characteristic of the sensor element, by producing an output indicating the change in the monitorable characteristic.

2. The leak monitoring fluid storage and dispensing apparatus according to claim 1, wherein the monitorable characteristic includes at least one property selected from the group consisting of resonant frequency, color, texture, chemical resistance, magnetic state, density, and chemical compositional state.

3. The leak monitoring fluid storage and dispensing apparatus according to claim 1, wherein the monitorable characteristic comprises resonant frequency.

4. The leak monitoring fluid storage and dispensing apparatus according to claim 1, wherein the sensor element comprises a piezoelectric material.

5. The leak monitoring fluid storage and dispensing apparatus according to claim 1, wherein the sensor element comprises a quartz microbalance.

6. The leak monitoring fluid storage and dispensing apparatus according to claim 1, wherein the sensor element comprises a surface acoustic wave device.

7. The leak monitoring fluid storage and dispensing apparatus according to claim 1, wherein the self-contained monitoring unit comprises an electrical power supply.

8. The leak monitoring fluid storage and dispensing apparatus according to claim 7, wherein the electrical power supply comprises a battery.

9. The leak monitoring fluid storage and dispensing apparatus according to claim 1, wherein the self-contained monitoring unit comprises a microprocessor and embedded controller assembly.

10. The leak monitoring fluid storage and dispensing apparatus according to claim 1, wherein the self-contained monitoring unit comprises a power supply and electronic circuitry constructed and arranged to operate in an intermittently active mode, and in a power-down mode between successive active mode events.

11. The leak monitoring fluid storage and dispensing apparatus according to claim 1, wherein the self-contained monitoring unit comprises an alarm producing said output indicating the change in the monitorable characteristic.

12. The leak monitoring fluid storage and dispensing apparatus according to claim 11, wherein said alarm comprises an audible alarm.

13. The leak monitoring fluid storage and dispensing apparatus according to claim 11, wherein said alarm comprises a visible alarm.

14. The leak monitoring fluid storage and dispensing apparatus according to claim 1, wherein the self-contained monitoring unit comprises a battery power supply providing at least four months operating time in service.

15. The leak monitoring fluid storage and dispensing apparatus according to claim 1, wherein the sensor element comprises a mass-sensitive piezoelectric device.

16. The leak monitoring fluid storage and dispensing apparatus according to claim 15, wherein the self-contained monitoring unit comprises an oscillator/mixer coupled in frequency response-geneting relationship to the piezoelectric device, said oscillator/mixer being coupled to a low-pass filter to produce an output frequency response signal, and a signal-processing microprocessor arranged in receiving relationship to the output frequency response signal, producing said output indicative of the change in the monitorable characteristic, wherein said monitorable characteristic comprises frequency response of the piezoelectric device.

17. The leak monitoring fluid storage and dispensing apparatus according to claim 16, wherein the piezoelectric device comprises a quartz microbalance.

18. The leak monitoring fluid storage and dispensing apparatus according to claim 16, wherein the piezoelectric device comprises a surface acoustic wave transducer.

19. The leak monitoring fluid storage and dispensing apparatus according to claim 1, wherein the said vessel comprises a high pressure gas cylinder.

20. The leak monitoring fluid storage and dispensing apparatus according to claim 1, wherein the contents of the portable vessel comprise a sorbent medium holding a gas for which the sorbent medium has sorptive affinity.

21. The leak monitoring fluid storage and dispensing apparatus according to claim 1, wherein the portable vessel is a high pressure gas cylinder comprising a manual valve hand wheel or pneumatic valve operator, and the leak detection device is secured to a neck portion of the cylinder, beneath the manual valve hand wheel or pneumatic valve operator.

22. The leak monitoring fluid storage and dispensing apparatus according to claim 1, wherein said self-contained monitoring unit comprises a DC battery.

23. The leak monitoring fluid storage and dispensing apparatus according to claim 1, wherein the self-contained monitoring unit comprises an AC power source.

24. The leak monitoring fluid storage and dispensing apparatus of claim 1 wherein the leak detection device is in proximity to a vessel locus including a structure selected from the group consisting of:joints, seams, ports, inlets, outlets and mechanical interconnections.

25. A vessel assembly, comprising:
 (a) a vessel; and
 (b) a leak detection device secured in detection proximity to the vessel, said leak detection device comprising:
  (i) a sensor element having at least one monitorable characteristic that changes upon exposure to the content of the vessel, wherein said sensor element is selected from the group consisting of: quartz crystal microbalance; SAW resonator; sorbent material absorber; and piezoelectric crystal; and
  (ii) a self-contained monitoring unit operatively coupled to the sensor element and arranged to respond to a change in the monitorable characteristic of the sensor element, by producing an output indicative of the change in the monitorable characteristic, the self-contained monitoring unit comprising a power supply and electronic circuitry constructed and arranged to operate in an intermittently active mode, and in a power-down mode between successive active mode events.

26. The vessel assembly according to claim 24, wherein the monitorable characteristic includes at least one property selected from the group consisting of resonant frequency, color, texture, chemical resistance, magnetic state, density, and chemical compositional state.

27. The vessel assembly according to claim 24, wherein the monitorable characteristic comprises resonant frequency.

28. The vessel assembly according to claim 25, wherein the sensor element comprises a piezoelectric material.

29. The vessel assembly according to claim 25, wherein the sensor element comprises a quartz microbalance.

30. The vessel assembly according to claim 25, wherein the sensor element comprises a surface acoustic wave device.

31. The vessel assembly according to claim 25, wherein the self-contained monitoring unit comprises an electrical power supply.

32. The vessel assembly according to claim 31, wherein the electrical power supply comprises a battery.

33. The vessel assembly according to claim 25, wherein the self-contained monitoring unit comprises a microprocessor and embedded controller assembly.

34. The vessel assembly according to claim 25, wherein the self-contained monitoring unit comprises an alarm producing said output indicating the change in the monitorable characteristic.

35. The vessel assembly according to claim 34, wherein said alarm comprises an audible alarm.

36. The vessel assembly according to claim 34, wherein said alarm comprises a visible alarm.

37. The vessel assembly according to claim 25, wherein the self-contained monitoring unit comprises a battery power supply providing at least four months operating time in service.

38. The vessel assembly according to claim 25, wherein the sensor element comprises a mass-sensitive piezoelectric device.

39. The vessel assembly according to claim 38, wherein the self-contained monitoring unit comprises an oscillator/mixer coupled in frequency response-generating relationship to the piezoelectric device, said oscillator/mixer being coupled to a low-pass filter to produce an output frequency response signal, and a signal-processing microprocessor arranged in receiving relationship to the output frequency response signal, producing said output indicative of the change in the monitorable characteristic, wherein said monitorable characteristic comprises frequency response of the piezoelectric device.

40. The vessel assembly according to claim 25, wherein said vessel comprises a high pressure gas cylinder.

41. The vessel assembly according to claim 25, wherein the contents of said vessel comprise a sorbent medium holding a gas for which the sorbent medium has sorptive affinity.

42. The vessel assembly according to claim 25, wherein said self-contained monitoring unit comprises a DC battery.

43. The vessel assembly according to claim 25, wherein the self-contained monitoring unit comprises an AC power source.

44. The vessel assembly according to claim 25, containing a high pressure gas.

45. The vessel assembly according to claim 25, containing a high pressure liquid.

46. The vessel assembly according to claim 25, further comprising a shroud overlying a valve assembly of said vessel, said shroud defining therein an enclosed volume, with said leak detection device disposed in said interior volume.

47. The vessel assembly according to claim 38, wherein the vessel comprises a high pressure gas cylinder with a valve head assembly including a valve hand wheel or pneumatic valve operator, wherein the leak detection device is secured to the valve head and underlies said manual valve hand wheel or pneumatic valve operator.

48. The vessel assembly according to claim 47, wherein said leak detection device has a lateral extent which is generally not in excess of the lateral extent of the manual valve hand wheel or pneumatic valve operator.

49. The vessel assembly according t o claim 25, wherein the leak detection device is secured to the vessel.

50. The vessel assembly of claim 25 wherein the leak detection device is secured to the vessel.

51. A leak monitoring fluid storage and dispensing apparatus comprising:
 (a) a portable vessel; and
 (b) a leak detection device mounted to the vessel, said leak detection device comprising:
  (i) a sensor element having at least one monitorable characteristic that changes upon exposure to the fluid content of the vessel, wherein said sensor element is selected from the group consisting of: a quartz crystal microbalance; a SAW resonator; a piezoelectric crystal; and a sorbent material absorber, and wherein said monitorable characteristic is selected from the group consisting of: resonant frequency, color, texture, chemical resistance, magnetic state, density, and chemical composition; and
  (ii) a self-contained monitoring unit operatively coupled to the sensor element and arranged to respond to a change in the monitorable characteristic of the sensor element, by producing an output indicating the change in the monitorable characteristic, the self-contained monitoring unit comprising a power supply and electronic circuitry constructed and arranged to operate in an intermittently active mode, and in a power-down mode between successive active mode events.

52. The leak monitoring fluid storage and dispensing apparatus of claim 51 wherein the leak detection device is secured to the vessel.

53. A leak detection device securable in detection proximity to a vessel, said leak detection device comprising:
(a) a sensor element comprising a mass-sensitive piezoelectric device having a monitorable characteristic that changes upon exposure to the content of the vessel; and
(b) a self-contained monitoring unit operatively coupled to the sensor element and arranged to respond to a change in the monitorable characteristic of the sensor element, by producing an output indicative of the change in the monitorable characteristic, said unit comprising an oscillator/mixer coupled in frequency response-generating relationship to the piezoelectric device, said oscillator/mixer being coupled to a low-pass filter to produce an output frequency response signal, and a signal-processing microprocessor arranged in receiving relationship to the output frequency response signal, producing said output indicative of the change in the monitorable characteristic, wherein said monitorable characteristic comprises frequency response of the piezoelectric device.

54. The leak detection device according to claim 53, wherein the piezoelectric device comprises a quartz microbalance.

55. The leak detection device according to claim 53, wherein the piezoelectric device comprises a surface acoustic wave transducer.

56. The leak detection device of claim 53 wherein the leak detection device is securable to the vessel.

57. A leak detection device constructed and arranged for securement to a neck portion of a gas cylinder, beneath a manual valve hand wheel or pneumatic valve operator of a high pressure gas cylinder, said leak detection device comprising:
(a) a sensor clement having a monitorable characteristic that changes upon exposure to the content of the vessel; and
(b) a self-contained monitoring unit operatively coupled to the sensor element and arranged to respond to a change in the monitorable characteristic of the sensor element, by producing an output indicative of the change in the monitorable characteristic.

58. A vessel assembly, comprising:
(a) a vessel; and
(b) a leak detection device secured in detection proximity to the vessel, said leak detection device comprising:
(i) a sensor element comprising a mass-sensitive piezoelectric device having a monitorable characteristic that changes upon exposure to the content of the vessel; and
(ii) a self-contained monitoring unit operatively coupled to the sensor element and arranged to respond to a change in the monitorable characteristic of the sensor element, by producing an output indicative of the change in the monitorable characteristic, the self-contained monitoring unit comprising a power supply and electronic circuitry constructed and arranged to operate in an intermittently active mode, and in a power-down mode between successive active mode events.

59. The vessel assembly according to claim 58, wherein the piezoelectric device comprises a quartz microbalance.

60. The vessel assembly according to claim 58, wherein the piezoelectric device comprises a surface acoustic wave transducer.

61. The vessel assembly of claim 58 wherein the leak detection device is secured to the vessel.

62. A vessel assembly, comprising:
(a) a vessel; and
(b) a leak detection device secured in detection proximity to the vessel, said leak detection device comprising:
(i) a sensor element comprising a mass-sensitive piezoelectric device having a frequency response that changes upon exposure to the content of the vessel;
(ii) a self-contained monitoring unit operatively coupled to the sensor element and arranged to respond to a change in the frequency response of the mass-sensitive piezoelectric device, by producing an output indicative of the change in the frequency response of the mass-sensitive piezoelectric device;
(iii) an oscillator/mixer coupled in frequency response-generating relationship to tile piezoelectric device, said oscillator/mixer being coupled to a low-pass filter to produce an output frequency response signal; and
(iv) a signal-processing microprocessor arranged in receiving relationship to the output frequency response signal, producing said output indicative of the change in the frequency response of the mass-sensitive piezoelectric device.

63. The vessel assembly of claim 62 wherein the leak detection device is secured to the vessel.

64. A vessel assembly, comprising:
(a) a high pressure gas cylinder; and
(b) a leak detection device secured to a neck portion of the cylinder, beneath a manual valve hand wheel or pneumatic valve operator, said leak detection device comprising:
(i) a sensor element having a monitorable characteristic that changes upon exposure to the content of the vessel; and
(ii) a self-contained monitoring unit operatively coupled to the sensor element and arranged to respond to a change in the monitorable characteristic of the sensor element, by producing an output indicative of the change in the monitorable characteristic.

65. A vessel assembly, comprising:
(a) a vessel;
(b) a leak detection device secured in detection proximity to the vessel, said leak detection device comprising:
(i) a sensor element having a monitorable characteristic that changes upon exposure to the content of the vessel; and
(ii) a self-contained monitoring unit operatively coupled to the sensor element and arranged to respond to a change in the monitorable characteristic of the sensor element, by producing an output indicative of the change in the monitorable characteristic; and
(c) a shroud overlying a valve assembly of the vessel, said shroud defining therein an enclosed volume, with said leak detection device disposed in said interior volume.

66. The vessel assembly of claim 65 wherein the leak detection device is secured to the vessel.

67. A vessel assembly, comprising:
(a) a high pressure gas cylinder and a valve head assembly including a valve hand wheel or pneumatic valve operator; and
(b) a self-contained leak detection device secured is secured to the valve head and underlying said manual valve hand wheel or pneumatic valve operator, said leak detection device comprising:

(i) a sensor element having a monitorable characteristic that changes upon exposure to the content of the vessel; and (ii) a monitoring unit operatively coupled to the sensor element and arranged to respond to a change in the monitorable characteristic of the sensor element, by producing an output indicative of the change in the monitorable characteristic.

68. The vessel assembly according to claim 67, wherein the leak detection device has a lateral extent which is generally not in excess of the lateral extent of the manual valve hand wheel or pneumatic valve operator.

69. A leak monitoring fluid storage and dispensing apparatus comprising:

(a) a fluid-containing vessel gas cylinder with a valve head assembly including a valve hand wheel or pneumatic valve operator; and (b) a leak detection device secured to the valve head in detection proximity to a mechanical interconnection of the vessel, and underlying the manual valve hand wheel or pneumatic valve operator, said leak detection device comprising:

(i) a sensor element having a monitorable characteristic that changes upon exposure to the fluid content of the vessel; and (ii) a self-contained monitoring unit operatively coupled to the sensor element and arranged to respond to a change in the monitorable characteristic of the sensor element, by producing an output indicating the change in the monitorable characteristic.

70. The leak monitoring fluid storage and dispensing apparatus of claim 69 wherein the leak detection device is secured to the vessel.

71. A leak detection device securable in detection proximity to a vessel, said leak detection device comprising:

(a) a sensor element comprises a mass-sensitive piezoelectric device having frequency response that changes upon exposure to the content of the vessel; and (b) a self-contained monitoring unit:

(i) operatively coupled to the sensor element and arranged to respond to a change in the frequency response of the mass-sensitive piezoelectric device, by producing an output indicative of the change in frequency response of the mass-sensitive piezoelectric device;

(ii) comprising an oscillator/mixer coupled in frequency response-generating relationship to the piezoelectric device and coupled to a low-pass filter to produce an output frequency response signal; and (iii) comprising a signal-processing microprocessor arranged to receive the output frequency response signal and to produce the output indicative of the change in the frequency response of the mass-sensitive piezoelectric device.

72. The leak detection device of claim 71 wherein the leak detection device is securable to the vessel.

73. A vessel assembly, comprising:

(a) a high pressure gas cylinder; and (b) a leak detection device secured in detection proximity to a neck portion of the cylinder, beneath a manual valve hand wheel or pneumatic valve operator, said leak detection device comprising:

(i) a sensor element having a monitorable characteristic that chances upon exposure to the content of the vessel; and (ii) a self-contained monitoring unit operatively coupled to the sensor element and arranged to respond to a change in the monitorable characteristic of the sensor element, by producing an output indicative of the change in the monitorable characteristic.

74. The vessel assembly of claim 25 wherein the leak detection device is secured to the vessel.

75. The vessel assembly of claim 74 wherein the leak detection device is secured to the neck portion of the vessel.

* * * * *

UNITED STATES PATENT AND TRADEMARK OFFICE
CERTIFICATE OF CORRECTION

PATENT NO : 6,079,252

DATED : June 27, 2000

INVENTOR(S) : Terry A. Tabler and Steven M. Lurcott

It is certified that error appears in the above-identified patent and that said Letters Patent is hereby corrected as shown below:

Column 11, line 35 change "monnitoring" to -- monitoring --
Column 12, line 37 change "response-geneting" to -- response-generating --
Column 18, line 21 omit "in detection proximity".
Column 18, line 26 change "chances" to -- changes --.

Signed and Sealed this

Seventeenth Day of April, 2001

Attest:

NICHOLAS P. GODICI

*Attesting Officer*  *Acting Director of the United States Patent and Trademark Office*